United States Patent [19]

Rivadeneira

[11] Patent Number: 6,077,969
[45] Date of Patent: Jun. 20, 2000

[54] PROCESS FOR PREPARING SUBSTITUTED VALINE AMIDE DERIVATIVES

[75] Inventor: Eric Rivadeneira, Overland Park, Kans.

[73] Assignee: Bayer Aktiengesellschaft, Leverkusen, Germany

[21] Appl. No.: 09/230,642

[22] PCT Filed: Jul. 21, 1997

[86] PCT No.: PCT/EP97/03907

§ 371 Date: Jan. 28, 1999

§ 102(e) Date: Jan. 28, 1999

[87] PCT Pub. No.: WO98/05633

PCT Pub. Date: Feb. 12, 1998

[30] Foreign Application Priority Data

Aug. 2, 1996 [DE] Germany .......................... 196 31 270

[51] Int. Cl.[7] ...................... C07C 269/04; C07C 271/14; C07C 271/18
[52] U.S. Cl. .............................................................. 560/29
[58] Field of Search .................. 560/24, 29, 30

[56] References Cited

U.S. PATENT DOCUMENTS 5,453,531   9/1995   Seitz et al. ................................ 560/29

FOREIGN PATENT DOCUMENTS 0 472 996   3/1992   European Pat. Off. .

OTHER PUBLICATIONS

M. R. Vernsten et al: "The Preparation of Some N–Carbethoxyamino Acids", Mar. 1953, DC US, 1320–1321, XP002046973, Journal of the American Chemical Society.

Database CAPLUS on STN, Acc. No. 108:38389, Chen et al., 'Diisopropylethylamine eliminates dipeptide formation during the acylation of amino acids using benzoyl chloride and some alkyl chloroformates.' Can. J. Chem (1987), 65(6), pp. 1224–1227 (abstract), 1987.

Primary Examiner—Johann Richter
Assistant Examiner—Brian J. Davis
Attorney, Agent, or Firm—Norris, McLaughlin & Marcus, P.A.

[57] ABSTRACT

A process is disclosed for preparing valine amide derivatives by reacting valine with chloroformic acid esters and phenethylamines in water.

7 Claims, No Drawings

PROCESS FOR PREPARING SUBSTITUTED VALINE AMIDE DERIVATIVES

The invention relates to valinamide derivatives and a process for their preparation.

The valinamide derivatives are known and have excellent effectiveness in pest control. In particular, they can be used as fungicides, especially in crop protection (EP-472 996).

It has now been found that the known valinamide derivatives can be prepared more simply and with higher yield and purity, it being possible to essentially dispense with the use of organic solvents.

The application thus provides a process for the preparation of compounds of the formula (I)

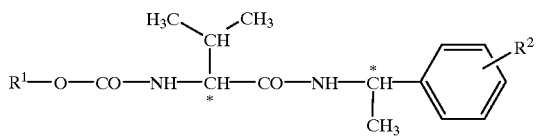

in which
R$^1$ is i-propyl or s-butyl, and
R$^2$ is chlorine, methyl, ethyl or methoxy,
in which
 a) an aqueous alkaline solution of L-valine is reacted with isopropyl chloroformate, and the resulting reaction products, after neutralization,
 b) are again, optionally in the presence of an organic solvent, in the presence of catalytic amounts of a tertiary amine reacted with isopropyl chloroformate, and then the resulting reaction products, optionally after the addition of organic solvents,
 c) are reacted with correspondingly substituted phenethylamine, optionally dissolved in organic solvents, at least one organic solvent being used in process step b) or process step c).

The valinamide derivatives obtainable by this process can be readily worked up and isolated and are produced in compact form with a high space/time yield.

The process according to the invention or the individual process steps a) and b) are preferably carried out in water as the sole solvent or diluent respectively.

The products of process steps a) and b) can be isolated and used for further reaction. However, the process is preferably carried out without intermediate isolation as a one-pot process, optionally with return of the mother liquor to a further batch or optionally with continuous processing.

For the process steps a) and b), isopropyl chloroformate is preferably used. The ester is preferably added to the corresponding solutions or reaction mixtures, the ester preferably being added in molar excess based on valine or the reaction product from process step a) and in total amounts of from 2 to 3 mol, based on 1 mol of valine.

The addition or reaction temperatures for process step a) are preferably from −20 to 80° C., in particular from 10 to 50° C., and for process step b) preferably from −20 to 40° C., in particular from 10 to 30° C. Process steps a) and b) are preferably carried out at room temperature, optionally with cooling of the exothermic reaction.

Process step a) is carried out in an alkaline medium, i.e. preferably in the presence of inorganic bases such as KOH and, in particular, NaOH. The base is in excess, in particular, in an amount from 1 to 3 mol, based on 1 mol of valine.

The neutralization in process step a) is preferably carried out using inorganic acids such as sulphuric acid and, in particular, hydrochloric acid, in particular to a pH of about 7.

Process step b) is carried out in the presence of catalytic amounts of a tertiary amine, preferably pyridine, methylpyridine, dimethylaminopyridine, triethylamine and/or, in particular, dimethylbenzylamine (Desmorapid DB®). In the present application, catalytic amounts are preferably taken to mean amounts of 1/10,000 to 1/100 mol of catalyst per mol of valine.

It is particularly important for process step c) and for subsequent work-up that the phenethylamines are dissolved in little organic solvent and brought to react only with the reaction products from process step b).

The solvents used are preferably acetic ester, methyl tert-butyl ether and, in particular, tert-amyl methyl ether (TAME). The amount of organic solvent used is preferably from 50 to 800 ml and, in particular, from 100 to 500 ml, based on 0.3 mol of the respective phenethylamine. The phenethylamines predissolved in this way are then preferably added to the reaction mixture from process step b), the amount of phenethylamine being equimolar or in slight excess relative to valine.

For better work-up of the target compounds produced in process step c), the reaction mixtures from process step c), are heated to temperatures of from 40° C. up to the boiling temperature of the respective organic solvent, optionally under pressure, until optimum separation of the organic phase from the aqueous phase is observed. The organic phase is then worked up by customary methods.

The products obtainable by the process according to the invention, which essentially consist of defined isomeric mixtures of the desired valinamide derivatives, can be used without further purification, e.g. as fungicides in crop protection.

Thus, in addition to the aforementioned merits, the process according to the invention has the advantages that the process in water as solvent and diluent, preferably from 50 to 500 g, in particular from 100 to 300 g of water, the desired products are produced in high yield and high purity. The following examples serve to illustrate the invention. The invention is not limited to the examples.

EXAMPLES

Example 1

35.8 g (0.305 mol) of L-valine are added to a mixture of 105 g of water and 63.6 g (0.716 mol) of 45% strength sodium hydroxide solution. The mixture is stirred until a clear solution forms.

Over the course of 2 hours 45.4 g (0.366 mol) of isopropyl chloroformate are then added dropwise at room temperature. The mixture is then stirred for 30 minutes. 37% strength hydrochloric acid is used to adjust the pH to 7.

0.4 g (0.003 mol) of Desmorapid DB® are then added to the reaction mixture. The mixture is then stirred for 15 minutes, and 38.4 g (0.31 mol) of isopropyl chloroformate are then added. The mixture is then stirred for a further hour.

A solution of 44.6 g (0.31 mol) of p-methylphenethylamine (3) in 200 ml of TAME (tert-amyl methyl ether) are then added over the course of two hours. A white solid immediately precipitates out, although the mixture remains stirrable.

The mixture is then heated to 70° C., phase separation is carried out at this temperature, and the organic phase is then washed with 100 ml of water. It is allowed to cool to 40° C. and filtered at this temperature. The suction filter cake is then washed with a little TAME and subsequently dried.

This gives 78.4 g of the product (content: 96.3%). This corresponds to a yield of 77.3% of theory.

The organic mother liquor gives after distilling of the solvent, 35.1 g of a residue, 43.7% of which is the desired product (yield: 15.7% of theory).

Comparative Example 2

35.8 g (0.305 mol) of L-valine are added to a mixture of 105 g of water and 63.6 g (0.716 mol) of 45% strength sodium hydroxide solution at room temperature. The mixture is stirred until a clear solution forms.

Over the course of 2 hours 45.4 g (0.366 mol) of isopropyl chloroformate are then added dropwise at room temperature. The mixture is then stirred for 30 minutes. 37% strength hydrochloric acid is used to adjust the pH to 7.

0.4 (0.003 mol) of Desmorapid DB® are then added to the reaction mixture. The mixture is then stirred for 15 minutes, and 38.4 g (0.31 mol) of isopropyl chloroformate are then added. The mixture is then stirred for a further hour.

44.6 (0.31 mol) of p-methylphenethylamine (3) are then metered in over two hours. The mixture is then stirred for one hour. During this time, the suspension formed becomes very thick, but still remains just stirrable. The mixture is then filtered with suction at room temperature, and the suction filter cake is then washed with 500 ml of water. Drying gives 99.5 g of a solid, 65.1% of which is the desired product. This corresponds to the yield of 66.3% of theory.

Example 3

35.8 g (0.305 mol) of L-valine are dissolved in a mixture of 105 g of water and 63.6 g (0.716 mol) of 45% strength sodium hydroxide solution at room temperature. The mixture is stirred until a clear solution forms.

45.4 g (0.366 mol) of isopropyl chloroformate (98.9% strength) are then added dropwise over the course of 2 hours. The mixture is then stirred for 30 minutes, and its pH is adjusted to 7 by adding 2.9 g of 37% strength hydrochloric acid.

650 ml of TAME and 0.4 g of Desmorapid DB® are added to the reaction medium. The mixture is then stirred for a further 15 minutes, and then 38.4 g (0.31 mol) of isopropyl chloroformate (98.9% strength) are added over the course of one hour.

The mixture is then stirred for one hour, and a solution of 44.6 g (0.31 mol) of p-methylphenethylamine (93.9% strength) in 130 ml of TAME is then metered in over the course of 2 hours. The mixture is then stirred for one hour, and 100 ml of sodium hydroxide solution (1N) are added to the suspension. At 55° C. the phases are separated. The organic phase is extracted once with 50 ml of water at 55° C. and then cooled to 0° C.

The mixture is then stirred for 30 minutes, and the solid is filtered off with suction under reduced pressure. The suction filter cake is then washed with a little TAME and dried in a vacuum drying cabinet. The filtrate is reduced on a rotary evaporator.

75.1 g of a suction filter cake are obtained, which has an active ingredient content of 99.7% (76.6% of theory).

The reduced mother liquor residue (17.2 g) has an active ingredient content of 56.6%.

Example 4

35.8 g (0.305 mol) of L-valine are dissolved in a mixture of 105 g of water and 63.6 g (0.716 mol) of 45% strength sodium hydroxide solution at room temperature. The mixture is stirred until a clear solution forms.

45.4 g (0.366 mol) of isopropyl chloroformate (98.9% strength) are then added dropwise over the course of 2 hours. The mixture is then stirred for 30 minutes, and its pH is adjusted to 7 by adding 3 g of 37% strength hydrochloric acid.

650 ml of TAME, 15.3 g of the mother liquor residue from Example 3 and 0.4 g of Desmorapid DB® are added to the reaction medium.

The mixture is then stirred for a further 15 minutes, and then 38.4 (0.31 mol) of isopropyl chloroformate (98.9% strength) are added over the course of one hour. The mixture is then stirred for an hour, and a solution of 44.6 g (0.31 mol) of p-methylphenethylamine (93.9% strength) in 130 ml of TAME is then metered in over the course of 2 hours. The mixture is then stirred for one hour, and 100 ml of sodium hydroxide solution (1N) are added to the suspension. At 55° C. the phases are separated. The organic phase is extracted once with 100 ml of water at 55° C. and subsequently cooled to 0° C. The mixture is then stirred for 30 minutes, and the solid is filtered off with suction under reduced pressure. The suction filter cake is then washed with a little TAME and dried in a vacuum drying cabinet. The filtrate is reduced on a rotary evaporator.

92.8 g of a suction filter cake are obtained, which has an active ingredient content of 97.4% (92.5% of theory).

What is claimed is:

1. Process for the preparation of compounds of the formula (I)

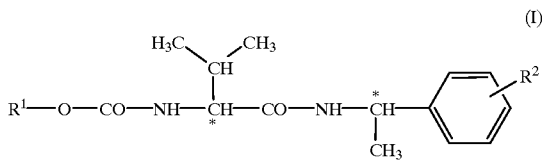

in which $R^1$ is i-propyl or s-butyl, and $R^2$ is chlorine, methyl, ethyl or methoxy, characterized in that a) an aqueous alkaline solution of L-valine is reacted with isopropyl chloroformate, and the resulting reaction products, after neutralization, b) are again reacted with isopropyl chloroformate in the presence of catalytic amounts of a tertiary amine and optionally in the presence of organic solvents, and then the resulting reaction products are optionally admixed with organic solvents and then c) reacted with correspondingly substituted phenethylamine, optionally dissolved in organic solvent, at least one organic solvent being used in process step b) or c).

2. Process according to claim 1, characterized in that the addition or reaction temperature of process step a) is from −20 to 80° C., process step b) is from −20 to 40° C. and process step c) is from 0 to 30° C.

3. Process according to claim 1, characterized in that the catalytically active tertiary amines in process step b) are pyridine, methylpyridine, dimethylaminopyridine, triethylamine and/or dimethylbenzylamine.

4. Process according to claim 1, characterized in that the organic solvent is acetic ester, methyl tert-butyl ether or tert-amyl methyl ether.

5. Process according to claim 1, characterized in that the amount of organic solvent is from 50 to 800 ml, based on 0.3 mol of the respective phenethylamine.

6. Process according to claim 1, characterized in that in process step c), after phenethylamine has been added, the reaction mixture is heated to from 40° C. to the boiling temperature of the respective organic solvent.

7. Process according to claim 1, characterized in that in process step c) p-methylphenethylamine is used.

* * * * *